United States Patent
El-Zehiry et al.

(10) Patent No.: US 9,918,700 B2
(45) Date of Patent: Mar. 20, 2018

(54) TUNING ULTRASOUND ACQUISITION PARAMETERS

(71) Applicants: Noha Youssry El-Zehiry, Plainsboro, NJ (US); Michelle xiaohong Yan, Princeton, NJ (US); Sara Good, Pleasanton, CA (US); Leo Grady, Millbrae, CA (US)

(72) Inventors: Noha Youssry El-Zehiry, Plainsboro, NJ (US); Michelle xiaohong Yan, Princeton, NJ (US); Sara Good, Pleasanton, CA (US); Leo Grady, Millbrae, CA (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 269 days.

(21) Appl. No.: 13/928,763

(22) Filed: Jun. 27, 2013

(65) Prior Publication Data
US 2014/0221832 A1 Aug. 7, 2014

Related U.S. Application Data (60) Provisional application No. 61/759,546, filed on Feb. 1, 2013.

(51) Int. Cl.
G06F 19/00 (2011.01)
A61B 8/00 (2006.01)
A61B 8/08 (2006.01)

(52) U.S. Cl.
CPC .............. *A61B 8/54* (2013.01); *A61B 8/5223* (2013.01); *A61B 8/585* (2013.01); *G06F 19/321* (2013.01); *G06F 19/345* (2013.01); *G06F 19/3406* (2013.01)

(58) Field of Classification Search
None
See application file for complete search history.

(56) References Cited

U.S. PATENT DOCUMENTS

| | | | |
|---|---|---|---|
| 7,288,068 B2 | 10/2007 | Bakircioglu et al. | |
| 7,578,792 B2 | 8/2009 | Lee et al. | |
| 7,591,788 B2 | 9/2009 | Phillips et al. | |
| 7,846,098 B2 | 12/2010 | Bakircioglu et al. | |
| 8,235,905 B2 | 8/2012 | Liu et al. | |
| 2007/0100475 A1* | 5/2007 | Korchinski | 700/28 |
| 2010/0240992 A1* | 9/2010 | Hao | 600/437 |
| 2010/0305441 A1* | 12/2010 | Lin et al. | 600/443 |

OTHER PUBLICATIONS

"Robust Object Recognition with Cortex-like Mechanisms", Tomoas Serre, et al. IEEE transactions on pattern analysis and machine intelligence, vol. 29. No. 3, Mar. 2007.*

(Continued)

*Primary Examiner* — Katherine Fernandez
*Assistant Examiner* — Marjan Saboktakin (57) ABSTRACT

Values for ultrasound acquisition parameters are altered in a manifold space. The number of parameters to be set is reduced using a manifold. Virtual parameters different than the acquisition parameters are used to alter the greater number of acquisition parameters. In a further use, optimum image settings may be obtained in an automated system by measuring image quality for feeding back to virtual parameter adjustment.

11 Claims, 2 Drawing Sheets

(56) References Cited

OTHER PUBLICATIONS

Ventura et al. Manifold learning examples—PCA, LLE and ISOMAP, Brighan Young University website, Oct. 14, 2008, pp. 1-8.*

Bronstein et al. ("Numerical geometry of non-rigid shapes", Stanford lecture series, 2009).*

J. B. Tenenbaum et al., "A Global Geometric Framework for Nonlinear Dimensionality Reduction," Science, vol. 290, pp. 2319-2323, 2000.

L. K. Saul et al., "Think Globally, Fit Locally: Unsupervised Learning of Low Dimensional Manifolds," Journal of Machine Learning Research 4, pp. 119-155, 2003.

M. Belkin et al., "Laplacian Eigenmaps and Spectral Techniques for Embedding and Clustering," In: Advances in Neural Information Processing Systems 14, MIT Press, pp. 585-591, 2001.

R. R. Coifman et al., "Diffusion maps," Applied and Computational Harmonic Analysis 21, pp. 5-30, 2006.

L. Cayton, "Algorithms for manifold learning," University of California at San Diego Tech. Rep., Abstract, 2005.

T. Serre et al., "Robust Object Recognition with Cortex-Like Mechanisms," IEEE Transactions on Pattern Analysis and Machine Intelligence, vol. 29, No. 3, pp. 411-426, 2007.

J. Mutch et al., "Object class recognition and localization using sparse features with limited receptive fields," International Journal of Computer Vision 80(1), pp. 45-57, 2008.

* cited by examiner

TUNING ULTRASOUND ACQUISITION PARAMETERS

RELATED APPLICATIONS

The present patent document claims the benefit of the filing date under 35 U.S.C. § 119(e) of Provisional U.S. Patent Application Ser. No. 61/759,546, filed Feb. 1, 2013, which is hereby incorporated by reference.

BACKGROUND

The present embodiments relate to medical diagnostic ultrasound imaging. In particular, values for acquisition parameters are established for imaging a patient using ultrasound.

Ultrasound imaging requires the adjustment of multiple acquisition parameters, such as the depth, focus, transmit frequency, and receive frequency (e.g., fundamental or harmonic imaging). The correct choice of values for the parameters impacts the quality of the output image. In practice, the default parameters recommended by the manufacturer may not always produce an image as good as could be produced. Due to differences in patients or other situational differences, the defaults may not be optimum.

The acquisition of a good quality image is a challenging task even for an experienced sonographer. Given the number of possible acquisition parameters that may be altered, determining the combination for imaging a patient is time consuming. Patients with large body habitus or large amounts of bowel gas may be particularly difficult to image. The abdominal scan time varies from 20-45 minutes. Moreover, the exam may become uncomfortable for the patient if the sonographer cannot set the acquisition parameters properly since sonographers tend to compensate by pressing against the patient's abdomen in an effort to obtain a better image.

BRIEF SUMMARY

By way of introduction, the preferred embodiments described below include methods, systems, instructions, and computer readable media for tuning acquisition parameters. Acquisition parameters are altered in a manifold space. There are two parameter spaces, the acquisition parameter space and the virtual parameter space. The number of parameters to be set in the actual parameter space is reduced using a manifold. Virtual parameters in the virtual parameter space different than the acquisition parameters are used to alter the greater number of acquisition parameters. In a further use, optimum image settings may be obtained in an automated system by measuring image quality for feeding back to virtual parameter adjustment.

In a first aspect, a method is provided for tuning ultrasound acquisition parameters. First ultrasound data is acquired with first values of a respective plurality of acquisition parameters. A processor projects the first values to a second value of at least one virtual parameter with a manifold relationship. The plurality of acquisition parameters is greater than a number of virtual parameters. The processor calculates a first quality score for the first ultrasound data. The second value is altered to a third value of the virtual parameter space. The altering is independent of the first quality score. The processor projects the third value to fourth values of the respective acquisition parameters. Second ultrasound data is acquired with the fourth values of the respective plurality of acquisition parameters. The processor calculates a second quality score for the second ultrasound data. The first and second quality scores are compared.

In a second aspect, a non-transitory computer readable storage medium has stored therein data representing instructions executable by a programmed processor for tuning ultrasound acquisition parameters. The storage medium includes instructions for selecting a setting of one or more manifold parameters different than and in a lower dimensional space than acquisition parameters, determining values for the acquisition parameters from a fewer number of the manifold parameters, the determining being a function of a manifold curve and a database of sample pairings of values of the manifold parameters and values of the acquisition parameters, and causing acquisition of ultrasound data with the values for the acquisition parameters.

In a third aspect, a system is provided for tuning ultrasound acquisition parameters. An ultrasound system is configurable to scan a patient with settings for scan variables. A memory is operable to store a manifold of the scan variables to a fewer number of manifold variables different than the scan variables. A processor is configured to cause the ultrasound system to scan with the settings for the scan variables determined with the manifold.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

The system includes one or more components. The first component is used to navigate the virtual parameter space to adjust the parameters. The second component is a quality assessment system that gives a score to the image acquired with the adjusted parameters.

Ultrasound image acquisition is a challenging task that requires the interrelated adjustment of several parameters. If the acquisition parameters are not properly chosen, the resulting image may have poor quality.

To provide an image with good quality, ultrasound acquisition parameters are simultaneously and/or adaptively tuned. A set of parameters to perform image acquisition are determined based on a manifold. The acquisition parameter dimensionality (numbers) is reduced to an intrinsic dimensionality by the manifold. The space of good acquisition parameter settings is reparameterized into a lower dimensional space or manifold that makes simultaneous parameter adjustment feasible. The parameter adjustment is performed in the lower dimensional space and the corresponding set of parameters in the original space is determined and used in the acquisition.

The tuning may be automatic or semi-automatic in response to simplified user control. For automation, the adjustment is performed iteratively until a best or sufficient quality image is captured. The image quality is assessed after each iteration to judge whether the quality is still improving or if the desired quality has already been reached. The image quality is used to define the direction of motion along or towards the manifold for subsequent adjustment. An example image quality measure is a trained Support Vector Machine (SVM) classifier based on Gabor filter features. In the semi-automatic mode, the quality assessment component is eliminated and the sonographer's judgment is used to assess the image quality. The auto-tuning is then reduced to a system where the user uses a single control key (knob) to adjust all the parameters.

The manifold reparameterization may be used independently or without the quality assessment. The simultaneous tuning of the acquisition parameters is performed without automated feedback. Rather than having the expert clinician adjust four different knobs on the machine to change the four different acquisition parameters, the clinician adjusts a fewer number (e.g., one) of knobs of one or more virtual or manifold parameters that simultaneously adjusts the four acquisition parameters.

Figure 1:
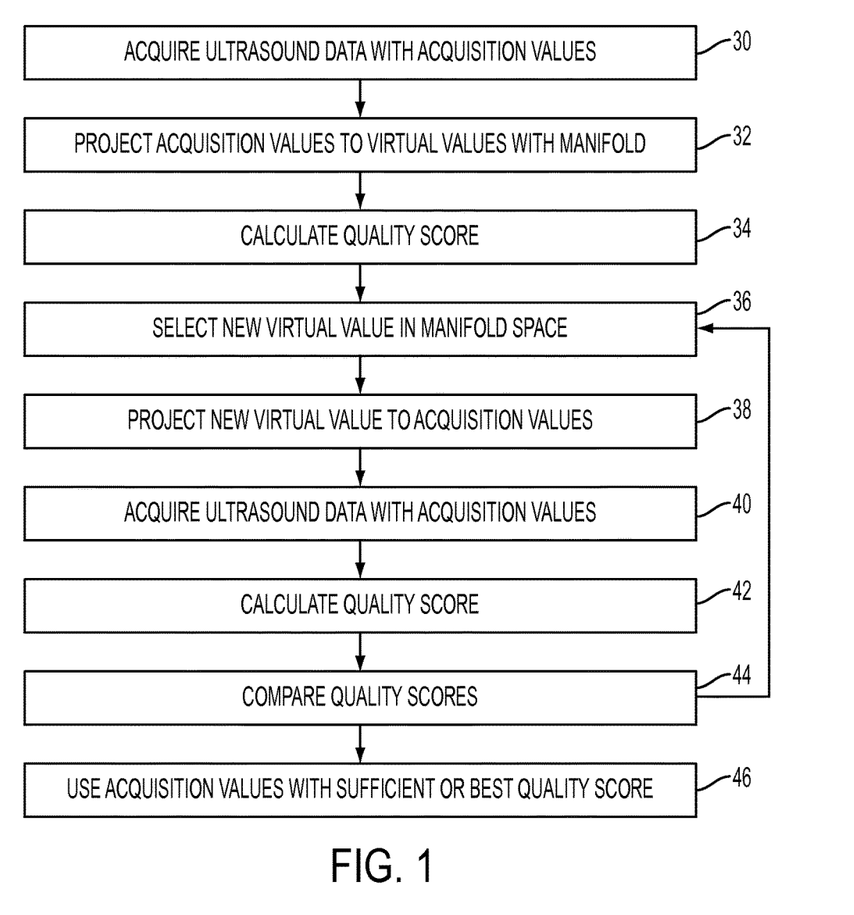
FIG. 1 is a flow chart diagram of one embodiment of a method for tuning ultrasound acquisition parameters.

FIG. 1 shows one embodiment of a method for tuning ultrasound acquisition parameters. The method is performed by the system of FIG. 3, a processor, or a different system. A processor of the system, processor of an ultrasound imaging system, or other processor implements software to perform one or more of the acts of FIG. 1. For example, the processor performs acts 32, 34, 38, and 42. The input is the starting values for acquisition parameters, such as defaults recommended by the scanner manufacturer or defined by a clinician. The output is a suggested set of values for imaging or an image resulting from scanning with the suggested set of values.

The user may compare quality, activate the scanning, input suggested acquisition parameter values, select the optimum acquisition parameter values, control adjustment of values of the virtual parameters along the manifold, or perform other actions. For more rapid operation to avoid patient discomfort and/or allow operation by a less experienced sonographer, one or more of the user acts are automated.

The method is performed in the order shown or a different order. For example, act 36 is performed before act 30. As another example, act 34 is performed prior to act 32. Additional, different, or fewer acts may be provided. For example, act 34 is not provided. As another example, acts 34 and 42-46 are not performed where manual alteration of the settings is used.

In act 30, ultrasound data is acquired. The ultrasound data is acquired by scanning in two or three dimensions (e.g., planar or volume scanning). The scanning is along scan lines. The scan lines may be acquired in any format, such as linear, curved linear, sector, curved sector, Vector®, curved Vector® and combinations thereof. The ultrasound data represents a region of a patient. The region includes any organ, tissue, bone, structure, or implant. By scanning the region, ultrasound images may be generated.

The ultrasound data is acquired as a frame of data. The frame represents an entire scan region, planar region, or volume region of the patient at a given time. Other groupings than frames may be used.

The frame of data includes samples representing the field of view or scanned region. The ultrasound data is beamformed data prior to detection, detected data prior to scan conversion (e.g., B-mode, flow-mode, velocity, energy, or variance), data after scan conversion, or data displayed as an image. The ultrasound data is image data for display, but image data may be data acquired to generate the image. The term image may be used to refer to an actually displayed image or to refer to locations and the frame of data for generating the display.

Various characteristics of the scan may be set. These acquisition or front-end parameters establish the scan. For example, the region of the patient to be scanned is determined, at least in part, by the depth and width of the scan. The depth along each scan line at which samples are obtained is set. As another example, the transmit frequency is set. Lower frequencies are associated with lower resolution imaging but greater penetration depth. In another example, the location of the focal point or focal depth is set. The acoustic energy from an array may have greater intensity due to coherence near the transmit focus than away from the focus. By setting the focal depth near a region of interest, better signal-to-noise ratio may be provided in that region of interest. In yet another example, the receive frequency is set. The receive frequency is the same as the transmit frequency (fundamental frequency) or a harmonic of the transmit frequency. Greater resolution but less depth may result from imaging with harmonic (e.g., second harmonic of the fundamental transmit frequency). Other acquisition parameters may include the aperture size, aperture synthesis, acoustic energy amplitude, acoustic energy phasing, flow sample count, pulse repetition interval or frequency, transmit waveform shape (e.g., square or sinusoid wave), number of cycles, beam synthesis, or other now known or later developed beamformer, front-end, or other acquisition parameter.

The acquisition parameters used for imaging may be based, at least in part, on the scan mode. Different modes may require the adjustment of parameters that are different from the ones stated in this embodiment. Various modes of ultrasound imaging are provided, such as B-mode, flow or Doppler mode, M-mode, spectral Doppler mode, harmonic mode, contrast agent mode, or tissue harmonic mode. For a given mode, application (e.g., region of the patient to be scanned), patient, and/or sonographer, different values of the acquisition parameters may be used as a default or as established by the sonographer.

For generating an image or obtaining a frame of data, the values of the acquisition parameters may be represented as a vector X of N dimensions. N represents the number of acquisition parameters that may be adjusted. For example, N is 4 for the focus depth, transmit frequency, receive frequency, and scan depth. In this example, the depth is 16 cm, the transmit frequency is 5 MHz, the receive frequency is the fundamental frequency (i.e., 5 MHz), and the focus is in the middle (i.e., 8 cm).

N may be a sub-set of available acquisition parameters. N is used for the acquisition parameters to be interrelated using the manifold. Other parameters may be altered or maintained outside of the manifold approach used herein. For example, line or beam synthesis is provided as a default and not changed using the manifold while the four acquisition parameters discussed in the example above are included in the manifold operation.

The settings may be altered while still scanning in a same mode. For example, default settings are used for B-mode imaging. One or more of the settings (e.g., focus, transmit frequency, receive frequency, and/or depth) are altered for continuing scan of the same region in the same mode. Some settings may be maintained at the same value.

To more conveniently change the settings, a manifold space is used for all or a sub-set of the acquisition parameters. In act 32, the values of the vector X or other acquisition parameters are projected to one or more virtual parameters with a manifold relationship. The dimensionality of the acquisition parameter space is reduced to the dimensionality of the manifold space, such as reducing four acquisition parameters to two virtual parameters (e.g., four dimensional acquisition space reduced to a two-dimensional manifold space). The number of values for a given image is reduced from four to two. A reduction from N by one or more is provided. Any number of virtual parameters less than N may be used.

The virtual parameters are not directly linked or are not acquisition parameters. Instead, the virtual parameters represent a relationship amongst combinations of acquisition parameters. Altering a value of one virtual parameter may be associated with changing values of any number of acquisition parameters. Similarly, altering a value of an acquisition parameter may be associated with changing any number of virtual parameters.

To project, a previously created manifold is used. The manifold relationship is learnt. Dimensionality reduction may be represented as: let $x_1, x_2, \ldots, x_n$ be a set of input data points in $R^D$. The objective is to find a lower dimensional representation $y_1, y_2, \ldots, y_n$ of the data in $R^d$ where d<D. If $x_i$ and $x_j$ are close to each other with respect to a certain proximity measure, then $y_i$ and $y_j$ should also be close to each other in the lower dimensional embedding. Manifold learning is the non-linear analog to principle component analysis.

Any manifold learning may be used, such as Isomap, Local Linear Embedding (LLE), Laplacian Eigen maps, or diffusion. The manifold is machine learnt, experimentally determined, or found by theoretical application. The Isomap approach uses of two main steps. The first step finds the geodesics distance between the input points $x_1, \ldots, x_n$ by calculating the shortest path on a k-nearest neighbor graph. The second step embeds in a lower dimensional manifold by finding the output points $y_1, \ldots, y_n$ such that the distance between $x_i$ and $x_j$ in the original high dimensional space is equal to the distance between $y_i$ and $y_j$ in the lower dimensional embedding. Local linear embedding works under the assumption that the manifold is locally smooth and hence the manifold may be approximated by the union of linear patches defined on a small neighborhood. The data point $x_i$ is expressed as a weighted convex combination of the elements in the nearest neighbor set N(i) in the sense that minimizes $\|x_i \Sigma_{j \in N(i)} W_{ij} x_j\|$. The weight matrix W captures the local geometry of the data that should be preserved when the data is embedded in a lower dimension, hence, the lower dimensional embedding y is obtained by optimizing $\Sigma_i \|y_i - \Sigma_j W_{ij} y_j\|^2$ with respect to $y_1, y_2, \ldots y_n \in R^d$. Laplacian Eigen maps borrows form spectral graph theory where the data is represented by a graph associated with a weight matrix W where $W_{ij}$ is the weight of the edge connecting $x_i$ to $x_j$. The Eigen values and the Eigen vectors of the graph Laplacian are used to investigate the wealth of the information in the input samples. The lower dimension y is obtained as the Eigen vectors associated with the non-zero Eigen values of $L_y = \lambda D_y$, where L is the graph Laplacian and D is the diagonal matrix with elements $D_{ii} = \Sigma_j W_{ij}$. Diffusion Map manifold learning is also inspired by the graph literature where the data points are represented by vertices on a graph and the edge connectivity is represented by a time dependent diffusion process. The diffusion matrix of the graph is calculated and the lower dimensional data representation is obtained as the Eigen vectors that correspond to the highest d Eigen values of the diffusion matrix.

To create the manifold, training data is obtained. The data is ultrasound data. Any number of scans, number of patients being scanned, patient locations (e.g., organs) being scanned, transducers being used to scan, or other variance may be provided in the set. For example, the set includes abdominal scans that cover seven different organs: aorta, liver, right kidney, left kidney, pancreas, spleen and gall bladder. The training data set is collected from 9 different subjects.

The scans are associated with desirable, good, best, or sufficient combinations of values of the acquisition parameters. Different combinations are included within the set. For example, to construct the manifold of the good parameter space, 32 different sets of four parameters (e.g., focus depth, transmit frequency, scan depth, and receive frequency) that produce images rated as "good" by a clinician expert are in the set of images.

A good parameter set may be used to scan different organs or different subjects. Some of the good images are acquired using the same scan depth, transmit frequency, focus depth, and receive frequency but differ in other parameters (e.g., gain or Dynamic Tissue Contrast Enhancement level), so are considered redundant since only a sub-set of acquisition parameters are being tuned. Other causes of reduction may be possible. Larger training sets may be used.

For manifold training in one embodiment using diffusion, a kernel, $\kappa(x, y)$ is defined, and the kernel matrix K is created such that $K_{i,j} = K(x_i, x_j) \forall x_j \in N(i)$. $\kappa(x, y)$ may be one of any various functions measuring proximity or relationship. For example, $K(x, y) = (-\exp(\|x-y\|^2))/\sigma$ where $\sigma=5$ and $|N(i)|=6$. A k-nearest neighbor graph, such as k=6, may be used with this Gaussian kernel. Other values of $\sigma$, k, and $|N(i)|$ may be used. The processor or other computational device creates the diffusion matrix by normalizing the rows of the kernel matrix to the range of [0,1], calculating the Eigen values and Eigen vectors of the diffusion matrix, and mapping to a d-dimensional diffusion space using the d dominant Eigen values. Any value (e.g., 1-3) may be used for d, such as d=2, as long as d is less than the number N of acquisition parameters for which the manifold is created.

The output of the manifold training is a database of pairings (x, y) where x is the high dimensional input feature vector and y is the low dimensional feature vector in the manifold space. This database is a sampling of the manifold for discrete values of settings of x and corresponding settings of y. In the example above, 32 different vectors x and corresponding 32 vectors y are paired. Other settings or vectors of x and/or y may be provided even though not included in the database.

The virtual parameters of the vector y may be related to each other or independently represent the manifold space. For example, the manifold obtained using the diffusion map for the example above is almost a 1-D manifold. The manifold may be approximated with a $4^{th}$ order polynomial or other curve fit to the manifold. The curve is stored or samples along the curve are stored as a database representing the manifold. By indicating a value for one of the virtual parameters, a unique value of the other virtual parameter is identified. In other embodiments, a given value of a virtual parameter may map to two or more values for another virtual parameter.

The learnt manifold, either the actual manifold or the fit approximation, is used to project values of the acquisition parameters to the lower dimensional virtual parameter space or manifold in act 32. For example, the pairings in the data base are used. Given acquisition parameter values x, the virtual parameter values y are calculated by look-up in the database, from the manifold curve, or from another representation of the manifold relationship.

Where the database does not include an exact match for the values of the acquisition parameters, the projection is performed using weighting. Weights, $\alpha$, are calculated using the acquisition parameter values. For example, to project the input X to the manifold, the distances to the closest k (e.g. k=5 or other value) points $X_1, \ldots, X_k$ recorded in the database representing the manifold relationship are determined. The input feature vector X may be expressed as a linear combination or approximation of the closest k vectors in the database as: $X \approx X' = \sum_{i=1}^{k} \alpha_i X_i$ where $\alpha = d_{k-i}/\sum_i d_i$, and $d_i$ is the distance between X and $X_i$. Other weight calculations may be used to determine a relationship of the input feature vector X of the values being used with the sample feature vectors stored in the database.

These weights from the acquisition parameter space are applied to the virtual parameter values of the manifold. The values stored in the database for the virtual parameters are weighted. The values to be weighted correspond to the paired k nearest neighbors identified in the acquisition parameter space. The projection Y is calculated using the linear combinations of $Y_1, \ldots, Y_k$ with the same ratios $\alpha_i, \ldots, \alpha_k$ calculated from the input feature vectors, so $Y = \sum_{i=1}^{k} \alpha_i Y_i$.

In act 34, a quality score is calculated. The quality of the ultrasound data, such as the data before generating an image or of the generated image, is determined for feedback in an automated process or to the user. The quality represents how good the ultrasound data obtained in act 30 is relative to ultrasound data in general.

Any classifier of quality may be used. For example, speckle, signal-to-noise, bandwidth, or other characteristic of the ultrasound data is measured. Alternatively, input from the user may be used to score.

In one embodiment, the score is calculated with a support vector machine (SVM) or other machine-learnt classifier for quality assessment. The SVM regressor scores the image. SVM is a classification and regression prediction tool that uses machine learning theory to maximize predictive accuracy while automatically avoiding an over-fit to the data. A classification task usually involves separating data into training and testing sets. Each instance in the training set contains one target value (i.e., the class labels) and several attributes (i.e., the features or observed variables). Based on the training data provided, the goal of SVM is to produce a model that predicts the target values of the testing data given only the test data attributes. For example, for a given training set with provided instance-label pairs $\{(x_i, y_i), i=1, \ldots, l\}$ where $x_i \in R$ and $y_i \in \{-1, 1\}$, the SVM requires a solution of the following optimization problem:

$$\min_{W,b,\epsilon} \{(1/2)W^T W + C\sum_{i=1}^{l} \epsilon_i\} \text{ subject to } y_i(W^T \varphi(x_i) + b) \geq 1 - \epsilon_i, \text{ and } \epsilon_i \geq 0$$

The function $\varphi(\ )$ maps the training vector $x_i$ onto a higher dimensional space. The SVM finds a linear separating hyper plane with the maximal margin in this higher dimensional space. C>0 is the penalty parameter of the error term. $K(x_i, x_j) \equiv \varphi(x_i)^T \varphi(x_j)$ is called the kernel function, which can be chosen from many basic forms, such as, linear or polynomial.

Other machine training may be used. The machine-trained classifier is any one or more classifiers. A single class or binary classifier, collection of different classifiers, cascaded classifiers, hierarchal classifier, multi-class classifier, model-based classifier, classifier based on machine learning, or combinations thereof may be used. Multi-class classifiers include CART, K-nearest neighbors, neural network (e.g., multi-layer perceptron), mixture models, or others. A probabilistic boosting tree may be used.

The same scoring is applied across patients, applications (e.g., liver imaging and heart imaging), and across transducers. In alternative embodiments, different scoring is provided for different applications, transducers, patients, or other aspect.

To train the ultrasound classifier for image quality, sample ultrasound data is acquired. For example, ultrasonic abdomen scans of the aorta, gall bladder, left kidney, liver, right kidney, pancreas and spleen are acquired. The training images are labeled as either good or bad or along a scoring scale (e.g., rated 1-10) by a clinician expert. For example, 192 images are used to train an SVM regressor. Another 280 images are used for testing performance. Other numbers of training and testing samples may be used.

The classifier is trained to operate on input features. Any input features may be used. The input to the classifier may include the ultrasound data itself, filtering results, results from image processing, and/or data from other sources than the ultrasound data (e.g., inputting the acquisition parameters or values for the parameters). Some example features are Haar wavelets or gradients.

In one embodiment, the input features are determined from a resolution pyramid. The ultrasound data is down sampled to different resolutions, providing different resolution levels of the same data in a pyramid data structure. For example, 4075 or other number of features are generated in a pyramid approach. An input image is converted to grayscale and sub-sampled such that the short width is less than a fixed size D, for example, D=280 pixels, while maintaining the aspect ratio of the original image. A three-dimensional (two spatial dimensions and one resolution dimension) image pyramid is then created with M resolution scales where each scale is a factor of $2^{(1/3)}$ smaller than the previous one. M is any value, such as 10, and other scale reduction factors may be used. Bi-cubic interpolation is used to calculate the data for each scale, but other down sampling may be used. The data for each resolution may be filtered. Filtering between resolution layers may be used. In other embodiments, the ultrasound data at the native resolution is used.

In an example feature set for scoring quality, a hierarchical approach that builds an increasingly complex and invariant feature representation alternates between template matching and maximum pool operations. Starting with an image layer of grayscale pixels, S1, C1, S2 and C2 layers are computed. "S" stands for simple layers where local filters are applied to compute higher order features. "C" stands for complex layers where maximum pooling is applied to the previous layer over limited regions. As a result, the number of units in C layers is reduced due to sub-sampling of the maximum pooling operation.

For example, a first S layer, S1, is provided by Gabor filtering the ultrasound data. The Gabor filtering of the image layer is provided along 4 (e.g., 0°, 45°, 90°, 135°) or other number of orientations. The S1 layer is a 4D structure, including the 3D pyramid shape, and has outputs of Gabor filtering at each location and scale. So there are a total of four pyramids with this structure in the S1 layer, each corresponding to one orientation. Gabor filters are described by:

$$G(x,y) = \exp(-(x_o^2 + y_o^2)/2\sigma^2)\cos(2\pi/\pi)x_o$$

where $x_o = x \cos \theta + y \sin \theta$ and $y_o = -x \sin \theta + y \cos \theta$. The parameters $\mu$, $\sigma$ and A are set to 0.3, 4.5 and 5.6 respectively, but other values may be used. Gabor filters with a size 11×11 are applied to all scales of the ultrasound data, but other size windows may be used. Other filtering functions may be used.

In a second layer of the hierarchal process to determine input features, a local invariance is calculated from an output of the Gabor filtering. The local invariance layer (C1) pools neighboring S1 units of the same orientation to create position and scale invariance over larger local regions. Random sampling may be used. For each orientation, for example, a 3D maximum filter with 10×10 in pixel and 2 in scale scans (e.g., random sampling) through each S1 orientation pyramid. Other size windowing may be used. The value $r_{C1}$ is a C1 unit representing the maximum of all S1 units that are covered (e.g., 10×10×2 window) by the maximum filter. This operation is represented as: $r_{C1}$=max through j=1, . . . m of $x_j$, where $\{x_1, \ldots, x_m\}$ are m S1 units within the window region. The resulting C1 layer is smaller in spatial extent, but is still a 4D structure as in S1. This pooling increases the tolerance to 2D transformations from layer S1 to C1. Other pooling functions may be used.

In a third layer of the hierarchal process, a template is matched to the local invariance. For an intermediate feature layer (S2), template matching is performed between a patch of C1 units and each of pre-selected N prototype patches. The prototype patches represent intermediate-level features—responses of the radial basis function with N patches. Any number of prototypes may be matched, such as prototypes with various sizes (4×4, 8×8, 12×12 or 16×16 with one scale). The prototypes are randomly sampled from the C1 layers. For each patch, the values of all C1 units within the patch are saved as a prototype. The values serve as a fuzzy template or another filter that runs through the C1 layer. For a given patch X from the previous C1 layer, the output $r_{S2}$ depends on the distance between the new input and a selected prototype P, in a Gaussian-like weighted fashion of: $r_{S2}=\exp(-\beta\|X-P_i\|)$, where $\beta$ defines the sharpness of the tuning. Both X and $P_i$ have dimensionality of n×n×4, where n∈{4, 8, 12, 16}. In addition to random sampling with various sized patches, learning and prototype selection of a set of N prototypes $\{P_i, i=1,N\}$ (or features) may improve the final classification performance. Other template matching or filtering may be used.

In a final layer, global invariance is calculated from an output of the matching. At the global invariance layer (C2), an N-dimensional feature vector is created. Each element of the feature vector is computed by taking a global maximum of all scales and orientations for each S2 type. So for each scale and orientation, the C2 layer keeps only the value of the best match and discards the rest. N features are randomly selected from the global invariance layer C2. For example, about 15 features are selected from an input image or set of ultrasound data. Other numbers of input features may be used.

The global invariance may be normalized. For example, the global invariance is normalized to zero mean and one variance. Normalization, other filtering, other processing, additional layers, fewer layers, different layers, or other approaches may be used to determine the input feature for the classification.

Using the quality classifier on a given set of ultrasound data, the input feature vector is calculated from the ultrasound data. The input feature vector is input to the trained classifier. The classifier (e.g., SVM classifier) outputs an image quality score. Any gradation of outputs for the classifier may be trained, such outputting on a scale of 1-10. In another embodiment, the classifier parameters (W, b, and $\epsilon$) are output. These parameters are stored from the training phase and represent the hyperplane (classifier) that gets used later in the testing state to score a newly acquired image that has not been used in the training phase. The parameters may represent the score or a score may be calculated from the parameters. The input image or ultrasound data is scored by application of the SVM regressor or other classifier.

In act 36, a new virtual parameter value is selected. One or more of the manifold parameters is set differently. This adjustment occurs in the lower dimensional space than the acquisition parameters. For example, one or more of the Y values is changed. This change is not a one-to-one change of a particular acquisition parameter, but is a change in the virtual parameter along the manifold or in the manifold space. Any number of virtual parameters may be simultaneously changed or changed prior to acquiring another or next set of ultrasound data.

The change is made by the user. For example, the user rotates a knob, alters a setting in a user interface, or indicates another change to be made for imaging. Rather than indicating a change in the focus, frequency, or depth, the user indicates a change in imaging generally or of the virtual parameter. In another embodiment, the change is automatic. A processor causes an incremental change to occur.

The alteration of the value of the virtual or manifold parameters is independent of the quality score. The quality score is not an explicit function of the set of virtual parameters, so is not used to calculate the value of the virtual parameters. The alteration may occur before calculating the score. The quality score may indicate which values correspond to better imaging than other values, but the values are not mapped from the score. A score of 7 does not indicate which virtual parameter values to use to obtain a better or worse score. The score may be used to determine a direction of change. If a previous increment leads to an improving score, then the next increment is in the same direction. If the previous increment led to a worse score, then the next increment is in a different (e.g., opposite) direction.

Any amount of change may be used. For example, the amount of change may be normalized to the range of the manifold. Any number of steps is used for incrementing. The size of a given step is determined by the range of the virtual parameter values in the database, is predetermined, or is set by the user.

One or more of the manifold parameters are incremented along or relative to the manifold relationship. For example, the increment is along the manifold curve representing likely good acquisition. The current values of the virtual parameter may be on the manifold curve. The next values of the virtual parameters are likewise selected to be on the manifold curve. If the current values are not on the manifold curve, the next values are selected to be on the curve near the current values or closer to the curve. Other criteria may be used.

In one embodiment, the values of the parameters are adjusted where the projected point Y from act 32 does not lie on the manifold. The closest point, $Y_m$, on the manifold is found. A unit vector $u_{YY_m}$ from Y in the direction of $Y_m$ is found. The step for the increment towards $Y_m$ is set to be one unit vector. Other step sizes may be used.

If the projected point Y lies on the manifold or the point $Y_m$ (i.e., after a previous increment to the manifold), the increment is a small step t along the manifold. The step size $t=(\max(x)-\min(x))/C$ where $\max(x)$ and $\min(x)$ are the manifold bounds (i.e., greatest and smallest values of the virtual parameter) along an axis and C is a constant (e.g., C=50). Other values for C, a predetermine step size, or other functions for determining the step size may be used. The step is in a selected, forward or backward direction. The step is towards $Y_{m+1}$, the closest point to Y that belongs to a Y sample stored in the database. After incrementing the value, the adjusted low-dimensionality parameters $Y_a$ are obtained.

In act 38, the values for the adjusted virtual parameters are projected to the acquisition parameter space. Values for the acquisition parameters are projected from the values for the virtual parameters. The low dimensional settings of the manifold are projected to the higher dimensional space of the acquisition parameters. By changing a fewer number of values (i.e., the number of virtual parameters), a greater number of acquisition parameters are changed and/or a greater range of combinations of values of the acquisition parameters are provided.

The projection is an inverse of the projection of act 32. The manifold, such as the manifold curve, and the database of sample pairings of values of the manifold parameters and values of the acquisition parameters are used to project. Where the incremented virtual parameters have values that are the same as a sample stored in the database, the corresponding values of the acquisition parameters are provided by look-up functions. From the database of pairings (x, y), the back projection $X_a$ that corresponds to the adjusted set of low-d parameters $Y_a$ is obtained. $X_a$ represent the new set of parameters in the original acquisition parameter space. If $Y_a$ does not belong to the database, the linear approximation or other neighbor strategy is used. Weights are calculated from nearest neighbors in the manifold space. The corresponding values of the acquisition parameters of the neighbors and the weights are used to determine the values of the acquisition parameters for $X_a$.

The values for the acquisition parameters are determined before acquiring another set of ultrasound data. Rather than adjust one acquisition parameter, image, adjust another, image, adjust the same again, or similar processes, multiple of the acquisition parameters are adjusted using the virtual parameter alteration prior to acquiring another set of ultrasound data. A more comprehensive adjustment more likely to lead to desirable image settings is performed in possibly one or at least fewer stages than separately incrementing through various possible combinations of values of the acquisition parameters. In some situations, one or more acquisition parameters may stay the same value despite a change to the virtual parameter values.

In act 40, another set of ultrasound data (e.g., image) is acquired. The projected values of the acquisition parameters are used for scanning the patient. The set of values $X_a$ of acquisition parameters are used to acquire a new image.

In act 42, a quality score is calculated for the new set of ultrasound data. The same classifier is used. The input features are determined from the new set of ultrasound data (e.g., image), and the classifier outputs the score based on the input features.

In act 44, the quality scores are compared. Any number of scores may be compared. In the example of FIG. 1, two quality scores are compared. One score is for the initial settings of the acquisition parameters and the other score is for the subsequent projected settings of the acquisition parameters. For later iterations, the two most recent or other combinations of scores are compared.

The comparison uses any function, such as finding a maximum or minimum. A difference or ratio may be determined. In one example, a higher one of the scores is determined where higher indicates better quality.

The settings of the acquisition parameters, the image, the virtual parameters values, or combinations thereof may be output to the user for the better quality. The user may use this information to further adjust or to select the desired settings.

The settings associated with the higher quality are used for subsequent scanning. For example, a threshold quality level is used. If the score is above the threshold, the setting of the acquisition parameters is complete and on-going scanning is performed.

If the score is not above the threshold or the user desires further quality improvement, the user may further adjust the values of the virtual parameters. Alternatively, the relative scores are used to control further alteration in an automated fashion.

The feedback from act 44 to act 36 represents repetition of the alteration, projection of the altered values in the manifold space to the values in the acquisition space, acquiring another set of ultrasound data, scoring, and comparison. The repetition provides testing of different settings to obtain a maximum or sufficient quality.

Figure 2:
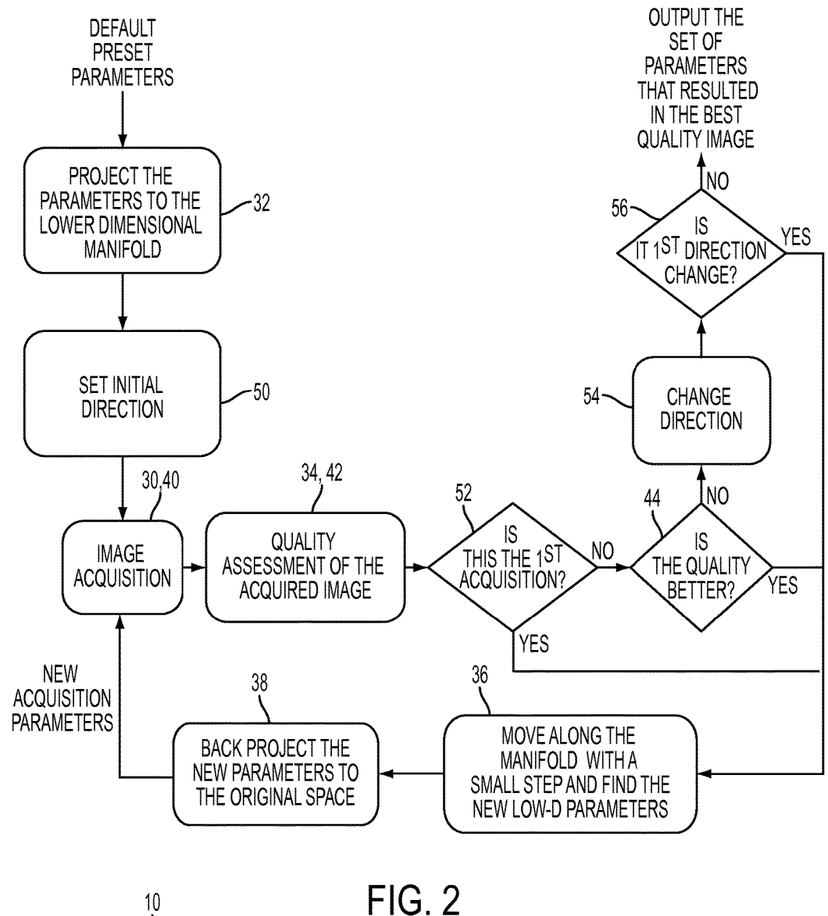
FIG. 2 is a flow chart diagram of another embodiment of a method for tuning ultrasound acquisition parameters.

The testing through repetition may be directed. FIG. 2 shows another embodiment of a method for tuning ultrasound acquisition parameters. The example of FIG. 2 deals with the direction of adjustment in the manifold space, so provides the acts in a different order with one or more additional acts than shown in FIG. 1. Other embodiments of the method are possible.

In act 50, an initial direction is set. The initial direction is predetermined, or otherwise selected. The initial settings of the acquisition parameter are projected to the manifold in act 32. Ultrasound data with the current settings is acquired in act 30. A score is calculated in act 34. In act 52, the process is tested for whether this is a first acquisition. If so, then the virtual parameter values are changed along the set direction in act 36, and the resulting values are back projected to the acquisition parameter space in act 38. New ultrasound data is acquired in act 40 and scored in act 42.

After a first iteration of adjusting the values of the virtual parameters in the selected direction in act 36, two sets of ultrasound data are acquired with different settings in acts 30 and 40, and scores are calculated in acts 34 and 42. In act 54 for these later iterations, the scores are compared in act 44. If the score is getting worse, the direction of alteration along the manifold is changed in act 54. Where this is the first change in direction, the process then proceeds to alteration of the virtual parameter values in act 36 for acquiring and scoring another set of ultrasound data. If the score of the new ultrasound data is getting worse and the direction of movement along the manifold has never been reversed, then the direction is reversed and the alteration, projection, acquisition and scoring acts are repeated.

If this is a subsequent change in direction above a threshold number of changes, the values for the acquisition parameters associated with the highest, or other indication of best score are used for further scanning. In an example with a curve function for the manifold, there are only two directions. If the direction of movement has been reversed during the process, then the automatic tuning process is terminated to prevent infinite looping along the manifold. Where the virtual parameter values map to exclusive options, the threshold is one change in direction. Processes, such as random sampling or step size changes may alternatively be used to rule out local maximum or non-exclusive mapping. Where the manifold is a surface or higher dimensional space, other sampling processes of settings of the virtual parameters may be used to find a sufficient or maximum.

Increments along the manifold represent gradual changes in the visual quality of the images from the ultrasound data. The manifold is a smooth surface, curve, or representation of the relationship amongst the acquisition parameters. Images from acquisitions associated with one increment will have more similar image quality than images from acquisitions separated by larger increment sizes or a greater number of increments. The process samples various virtual parameter settings to find a desired image quality in a gradual process, but random or other less gradual sampling may be used.

In act 46 of FIG. 1, the alteration of the acquisition parameter values is terminated. An output set of acquisition parameters values is used for generating ultrasound medical diagnostic images. The images are associated with a best or sufficient quality for the given scanning situation. The acquired images are displayed, transmitted, or saved for diagnosis.

Figure 3:
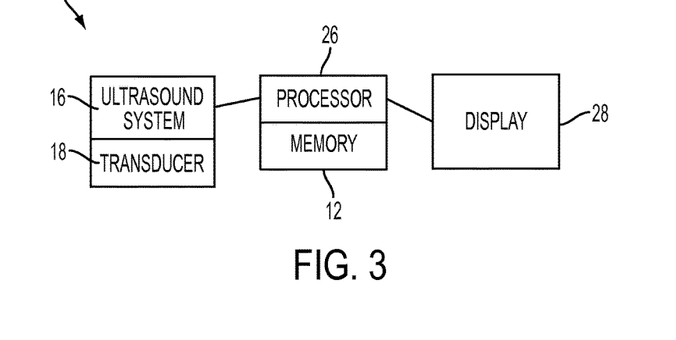
FIG. 3 is a block diagram of one embodiment of a system for tuning ultrasound acquisition parameters.

FIG. 3 shows a system for tuning ultrasound acquisition parameters. The system 10 includes an ultrasound system 16, a transducer 18, a processor 20, a memory 22, and a display 24. The transducer 18 is used by the ultrasound system 16 to scan a patient, and the processor 20 sets the values of variables for scanning. Additional, different, or fewer components may be provided. For example, a network or network connection is provided, such as for networking with a medical imaging network or data archival system. As another example, a user interface is provided.

The processor 20, memory 22, and display 24 are part of a medical imaging system, such as the diagnostic or therapy ultrasound system 16, or other system. Alternatively, the processor 20, memory 22 and/or display 24 are part of an archival and/or image processing system, such as associated with a medical records database workstation or server. In other embodiments, the processor 20, memory 22, and/or display 24 are a personal computer, such as desktop or laptop, a workstation, a server, a tablet, a network, or combinations thereof.

The ultrasound system 16 is any now known or later developed ultrasound imaging system. For example, the ultrasound system 16 includes the transducer 18 for converting between acoustic and electrical energies. Transmit and receive beamformers relatively delay and apodize signals for different elements of the transducer 18. The beamformers operate at transmit and receive frequencies to sample over scan lines at various depths. The transmit beamformer focuses to one or more locations along each scan line, and the receive beamformer operates with a dynamic receive focus that changes as a function of time to sample along the scan line. B-mode, Doppler, or other detection is performed on the beamformed signals. A scan converter, memory, three-dimensional imaging processor, and/or other components may be provided.

The transducer 18 is a one-, two-, or multi-dimensional array of piezoelectric or capacitive membrane elements. For example, the transducer 18 is a one-dimensional array of elements within a handheld probe. In another embodiment, the transducer 18 is part of a probe for use within the patient, such as a transesophageal or cardiac catheter probe.

The memory 22 is a graphics processing memory, video random access memory, random access memory, system memory, cache memory, hard drive, optical media, magnetic media, flash drive, buffer, database, combinations thereof, or other now known or later developed memory device for storing data or video information. The memory 22 is part of an imaging system, a computer associated with the processor 20, a database, another system, a picture archival memory, or a standalone device.

The memory 22 stores data representing a region of a patient. A single frame or multiple frames of data may be stored. The region is a two or three-dimensional region. The region is of any part of the patient, such as a region within the chest, abdomen, leg, head, arm, or combinations thereof. The data is from scanning the region with ultrasound. The data represents the patient prior to, during, or after treatment.

Settings or values of scan variables are stored in the memory 22. For example, the depth of the scan region, the focal depth along one or more scan lines, the transmit frequency, and the receive frequency are stored. Where data is acquired with different settings, the settings for the different sets of data are stored.

A manifold of the scan variables relating the scan variables to a fewer number of manifold variables different than the scan variables is stored. A database of samplings on the manifold or pairs relating values of the manifold variables to values of the scan variables is stored. Different settings of the scan variables paired with different values of the manifold variables represents the manifold. A fit curve, surface, or n-dimensional object may be stored as the manifold.

A classifier for scoring is stored in the memory 22. The matrix representing the machine-learned classifier is maintained in the memory for access by the processor 20. Functions and/or data for determining input features are stored.

The memory 22 may store processed data. For example, the results of filtering, input feature calculations, scoring, increments, vectors, constants, variables, values of variables, or other information are stored. Thresholds, weights, or other information may be stored.

The memory 22 or other memory is alternatively or additionally a computer readable storage medium storing data representing instructions executable by the programmed processor 20 for tuning ultrasound scan variables. The instructions for implementing the processes, methods and/or techniques discussed herein are provided on non-transitory computer-readable storage media or memories, such as a cache, buffer, RAM, removable media, hard drive or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts, or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The display 24 is a monitor, LCD, projector, plasma display, CRT, printer, or other now known or later developed devise for outputting visual information. The display 24 receives images, graphics, or other information from the processor 20, memory 22, or ultrasound system 16.

One or more images representing the scanned patient are displayed. The image represents a sufficient or best quality as determined by variation of manifold parameters in the manifold space. Images associated with different settings of the scan variables may be displayed. Alternatively, images associated with the automatically tuned scan variables are displayed. Ultrasound data acquired for tuning is not used for displaying images, but may be used.

The images may be two-dimensional images. A planar or area region is represented in the image. In other embodiments, a volume is represented. Multiple planar scans representing different planes are stacked or used to form a volume. An image is rendered from the volume.

The processor 20 is a general processor, central processing unit, control processor, graphics processor, digital signal processor, three-dimensional rendering processor, image processor, application specific integrated circuit, field programmable gate array, digital circuit, analog circuit, combinations thereof, or other now known or later developed device for tuning scan variables. The processor 20 is a single device or multiple devices operating in serial, parallel, or separately. The processor 20 may be a main processor of a computer, such as a laptop or desktop computer, or may be a processor for handling some tasks in a larger system, such as in an imaging system. The processor 20 is configured by instructions, design, hardware, and/or software to be able to perform the acts discussed herein, such as projecting between a manifold space and a scan variable space and ranking data.

In one embodiment, the processor 20 is configured to select one or more of the values of the manifold variables and project the one or more values to the settings of the scan variables with the manifold. The selection and projection are provided for any tuning process, whether manual, automatic, or semi-automatic. By altering or adjusting in the manifold space, a lower dimensional change is used to alter the higher dimensional scan variable space.

The processor 20 is configured to cause the ultrasound system 16 to scan with the settings for the scan variables determined with the manifold. The ultrasound system 16 is caused to scan with different settings at different times, such as in a repeating or iterative process to sample the manifold and/or determine a sufficient or optimum set of settings.

The processor 20 is configured to calculate quality levels corresponding to the different settings. Any classifier, scoring, ranking, or measure may be used to calculate quality level. A group of the settings is selected based on the quality levels. The processor 20 uses the manifold without being based on the quality level. The quality level may be used to determine whether or when to use the manifold, but the values for the manifold and projection from the manifold are independent of the quality level.

In one embodiment, the ultrasound system 16 is configured to scan the aorta. Ultrasound data is acquired using a default set of parameters recommended by the scanner manufacturer for the abdomen. In some cases, the default parameter may result in poor image quality that needs improvement for diagnosis. Using the processor 20, slight adjustments in the set of the parameters are made by taking steps towards the manifold of the good parameter space until reaching the manifold. The parameters are adjusted further by taking infinitesimal steps along the manifold and projecting back to the high dimensional space to find the corresponding set of values for scan variables. These steps are repeated until a good quality image is captured.

The convention used for the grading may be as follows: grades 0-6 are given to a poor quality image that cannot be used for diagnosis and treatment, grades 7-8 are given to an acceptable image that can be used in the clinic for diagnosis and treatment, but may not be the best image and a better image may be obtained if the parameters are better tuned, and grades 9-10 are given to a high quality images where no or little further improvement is necessary and that the sonographer may have deliberately chosen. The variability between 9-10 may reflect variability in expert clinician's preferences (i.e., an image that is graded 9 by one expert clinician may have been graded 10 by a different expert).

The auto tuning algorithm implemented by the processor 20 operates for different subjects and different organs. Images are acquired from different subjects with varying body mass indices. The tuning works equally well for these different image acquisition scenarios. Different user presets may be used initially. The auto tuning algorithm is capable of providing a set of parameters that yield a good quality image regardless of the starting point. In one example, a fatty liver requiring deep penetration is scanned. The auto tuning sets values for the scan variables appropriate for this situation and different than appropriate for the kidney. The same algorithm may tune for these different imaging contexts. The tuning is capable of changing the mode of operation from Tissue Harmonic Imaging (THI) to general B-mode fundamental imaging and produces the correct frequency, depth, and focus for imaging in either mode.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for tuning ultrasound acquisition parameters, the method comprising:

acquiring by scanning a patient with ultrasound using a transducer of an ultrasound system, first ultrasound data with a first set of acquisition parameters of a plurality of sets of acquisition parameters;

calculating, with a processor, a first quality score for the first ultrasound data;

projecting, with the processor, the first set of acquisition parameters to first coordinates in a manifold space, wherein the manifold space comprises a plurality of coordinates for each of the plurality of sets of acquisition parameters, wherein the manifold space describes a relationship between each of the plurality of sets of acquisition parameters, wherein the dimensionality of the coordinates of the manifold space is lower than a number of acquisition parameters in each of the sets of acquisitions parameters;

selecting second coordinates adjacent on the manifold space to the first coordinates; the second coordinates corresponding to a second set of acquisition parameters of the plurality of sets of acquisition parameters;

acquiring, by the ultrasound system using the transducer to scan the patient with ultrasound, second ultrasound data with the second set of acquisition parameters calculating, with the processor, a second quality score for the second ultrasound data;

comparing the first and second quality scores;

comparing the second quality score to a quality threshold level;

imaging the patient by the ultrasound system using the second set of acquisition parameters when the second quality score is equal to or above the quality threshold level;

selecting, when the second quality score is lower than the quality threshold level, third coordinates adjacent on the manifold space to the second coordinates or first coordinates, the third coordinates adjacent to the first coordinates when, based on the comparison of the first and second quality scores, the first quality score is determined to be higher than the second quality score, and the third coordinates adjacent to the second coordinates when the second quality score is determined to be higher than the first quality score; the third coordinates corresponding to a third set of acquisition parameters of the plurality of sets of acquisition parameters;

acquiring, by the ultrasound system using the transducer to scan the patient with ultrasound, third ultrasound data with the third set of acquisition parameters;

calculating, with the processor, a third quality score for the third ultrasound data determining, by the processor, that the third quality score is equal to or higher than the quality threshold level; and when the third quality score is equal or above the quality threshold level, imaging the patient, by the ultrasound system, using the third set of acquisition parameters when the third quality score is lower than the quality threshold level, repeating the steps of:

selecting next corresponding coordinates adjacent on the manifold space to the current coordinates or previous coordinates, the next corresponding coordinates corresponding to a next set of acquisition parameters of the sets of acquisition parameters and the next corresponding coordinates adjacent to the previous coordinates when the previous quality score is higher than the current quality score, and the next corresponding coordinates adjacent to the current coordinates when the current quality score is higher than the previous quality score;

acquiring, by the ultrasound system using the transducer to scan the patient with ultrasound, next corresponding ultrasound data with the next corresponding set of acquisition parameters;

calculating, with the processor, a next corresponding quality score;

determining, by the processor, that the next corresponding quality score to the threshold level; and comparing the next corresponding quality score to the current quality score;

until a respective next corresponding quality score is equal or above the quality threshold level; and scanning, by an ultrasound system, the patient using the set of acquisition parameters that corresponds to the quality score that is equal or above the threshold quality score.

2. The method of claim 1 wherein acquiring the first and second ultrasound data comprises acquiring the first, second, and each next corresponding ultrasound data representing a two or three-dimensional region of a patient in a same scan mode.

3. The method of claim 1 wherein acquiring the first, second, and each next corresponding ultrasound data comprises acquiring B-mode data.

4. The method of claim 1 wherein acquiring the first, second, and each next corresponding ultrasound data comprises acquiring with the acquisition parameters being depth, frequency, focus location, and fundamental or harmonic reception, the first coordinates differing from the second coordinates and each next corresponding coordinates for at least one of the acquisition parameters.

5. The method of claim 1 wherein calculating the first, second, and each next corresponding quality scores comprises calculating with a support vector machine.

6. The method of claim 1 wherein calculating the first, second, and each next corresponding quality scores comprises determining input features from resolution pyramids derived from the first, second, and each next corresponding ultrasound data, respectively, and applying the input features to a machine-learnt classifier.

7. The method of claim 6 wherein determining the input features comprises:

Gabor filtering the first, second; and each next corresponding ultrasound data;

calculating local invariance from an output of the Gabor filtering; matching a template to the local invariance; and calculating a global invariance from an output of the matching.

8. The method of claim 1 wherein selecting second, and each next corresponding coordinates adjacent on the manifold space comprises incrementing along the manifold space.

9. The method of claim 1 wherein the second, and each next corresponding coordinates are selected as a function of user input.

10. A system for tuning ultrasound acquisition parameters, the system comprising:

an ultrasound system configurable to scan a patient using a first set of scan variables and generate a first image in response to the scan;

a memory operable to project in a manifold space the first set of scan variables as first coordinates in the manifold space, wherein the manifold space comprises a plurality of coordinates for each of a plurality of sets of scan variables including the first set of scan variables, wherein the manifold space describes a relationship between the variables in each of the plurality of sets of scan variables, wherein the dimensionality of coordinates of the manifold space is lower than a number of scan variables in each of the sets of scan variables; and a processor configured to select second coordinates adjacent on the manifold space to the first coordinates; the second coordinates corresponding to a second set of scan variables of the plurality of sets of scan variables;

wherein the ultrasound system is further configured to scan a patient with the second set of scan variables and generate a second image in response to the scan;

wherein the processor is configured to calculate a first quality score for the first image and a second quality score for the second image; wherein the processor is further configured to compare the first quality score and second quality score to a quality threshold, the ultrasound system is configured to image the patient by the ultrasound system using the second set of scan variables when the second quality score equal to or above a quality threshold level; and the processor is configure to select, when the second quality score is lower than the quality threshold level, third coordinates adjacent on the manifold space to the second coordinates or first coordinates, the third coordinates adjacent to the first coordinates when the first quality score is higher than the second quality score, and the third coordinates adjacent to the second coordinates when the second quality score is higher than the first quality score, the third coordinates corresponding to a third set of acquisition parameters of the plurality of sets of acquisition parameters, wherein the ultrasound system is configured using the transducer to scan the patient using the third set of acquisition parameters, and generate a third image in response to the scan, wherein the processor is configured to calculate a third quality score for the third image, and compare the third quality score with the quality threshold level;

when the third quality score is equal to or higher than the quality threshold level, the ultrasound system images the patient using the third set of acquisition parameters;

when the third quality score is lower than the quality threshold level, repeating the steps of:

selecting next corresponding coordinates adjacent on the manifold space to the current coordinates or previous coordinates, the next corresponding coordinates corresponding to a next set of acquisition parameters of the sets of acquisition parameters and the next corresponding coordinates adjacent to the previous coordinates when the previous quality score is higher than the current quality score, and the next corresponding coordinates adjacent to the current coordinates when the current quality score is higher than the previous quality score;

the ultrasound system is further configured to scan a patient with the next corresponding set of acquisition parameters and generate a next corresponding image in response to the scan;

wherein the processor is configured to calculate a next corresponding quality score for the next corresponding image;

wherein the processor is configured to compare the next corresponding quality score to the quality threshold; and wherein the processor is further configured to compare next corresponding quality score to the current quality score;

until a respective next corresponding quality score is equal or above the quality threshold; and wherein the ultrasound system is configured to scan the patient using the set of acquisition parameters that corresponds to the quality score that is equal or above the threshold quality.

11. A Method for tuning ultrasound acquisition parameters, the method comprising:

acquiring, by a processor, a first image of a patient using a first set of scan variables that corresponds to a first set of coordinates in a manifold space, wherein the manifold space comprises a plurality of sets of coordinates, each set of coordinates of the plurality of sets of coordinates corresponding to a set of scan variables, wherein the dimensionality of coordinates of the manifold space is lower than a number of scan variables in each of the sets of scan variables;

acquiring, by the processor, a second image of the patient using a second set of scan variables that corresponds to a second set of coordinates in the manifold space;

scoring, by the processor, the first and second image, resulting in a first image score and a second image score;

wherein when the second image score is higher than the first image score, the processor selects a third coordinate in the manifold space adjacent to the second coordinate; wherein when the first image score is higher than the second image score, then the processor selects a third coordinate in the manifold space adjacent to the first coordinate;

scoring, by the processor, the third image resulting in a third image score; and when the third quality score is equal or above the quality threshold level, imaging the patient, by the ultrasound system, using the third set of acquisition parameters;

when the third quality score is lower than the quality threshold level, repeating the steps of:

selecting next corresponding set of coordinates adjacent on the manifold space to the current set of coordinates or previous set of coordinates, the next corresponding set of coordinates corresponding to a next set of acquisition parameters of the sets of acquisition parameters and the next corresponding set of coordinates adjacent to the previous coordinates when the previous quality score is higher than the current quality score, and the next corresponding set of coordinates adjacent to the current set of coordinates when the current quality score is higher than the previous quality score;

acquiring, by the ultrasound system using the transducer to scan the patient with ultrasound, next corresponding ultrasound data with the next corresponding set of acquisition parameters;

calculating, with the processor, a next corresponding quality score;

comparing, by the processor, the next corresponding quality score to the threshold level; and comparing the next corresponding quality score to the current quality score;

until a respective next corresponding quality score is equal or above the quality threshold level, or a maximum number of iterations are reached; wherein the maximum number of iterations are inputted by the user;

when a respective next corresponding quality score is equal or above the quality threshold level: scanning, by an ultrasound system, the patient, using the set of acquisition parameters that corresponds to the quality score that is equal or above the threshold quality score;

when the maximum number of iterations have been reached but a respective next corresponding quality score is still lower than the quality threshold, scanning, by an ultrasound system, the patient, using the set of acquisition parameters that corresponds to the highest quality score among the first, second, third and each next corresponding quality scores lower or equal to the maximum number of iterations.

* * * * *